(12) United States Patent
Kosteroglou et al.

(10) Patent No.: US 9,725,763 B2
(45) Date of Patent: Aug. 8, 2017

(54) METHODS AND COMPOSITIONS FOR NANOSTRUCTURE-BASED NUCLEIC ACID SEQUENCING

(71) Applicant: Eve Biomedical, Inc., Redwood City, CA (US)

(72) Inventors: Theofilos Kosteroglou, Hillsborough, CA (US); Stephanos Papademetriou, Sunnyvale, CA (US)

(73) Assignee: Eve Biomedical, Inc., Redwood City, CA (US)

( * ) Notice: Subject to any disclaimer, the term of this patent is extended or adjusted under 35 U.S.C. 154(b) by 0 days.

(21) Appl. No.: 14/185,469

(22) Filed: Feb. 20, 2014

(65) Prior Publication Data

US 2014/0235462 A1    Aug. 21, 2014

Related U.S. Application Data

(60) Provisional application No. 61/766,925, filed on Feb. 20, 2013.

(51) Int. Cl.
    *C12Q 1/68* (2006.01)
(52) U.S. Cl.
    CPC .................................. *C12Q 1/6869* (2013.01)
(58) Field of Classification Search
    None
    See application file for complete search history.

(56) References Cited

U.S. PATENT DOCUMENTS

| | | | |
|---|---|---|---|
| 5,693,489 A | 12/1997 | Studier et al. | |
| 6,015,714 A * | 1/2000 | Baldarelli ............ | C07K 14/705 435/4 |
| 7,556,922 B2 * | 7/2009 | Block et al. ................. | 435/6.11 |
| 8,574,840 B2 | 11/2013 | Kotseroglou | |
| 9,017,937 B1 * | 4/2015 | Turner ................. | C12Q 1/6869 435/6.1 |
| 2002/0067417 A1 | 6/2002 | Tan et al. | |
| 2002/0172953 A1 | 11/2002 | Mirkin et al. | |
| 2003/0194740 A1 | 10/2003 | Williams | |
| 2006/0063171 A1 * | 3/2006 | Akeson ............ | B01L 3/502707 435/6.11 |
| 2007/0077575 A1 | 4/2007 | McAllister et al. | |
| 2007/0148645 A1 * | 6/2007 | Hoser ...................... | B82Y 5/00 435/6.12 |
| 2008/0020392 A1 | 1/2008 | Block et al. | |
| 2009/0208957 A1 | 8/2009 | Korlach et al. | |
| 2010/0035260 A1 * | 2/2010 | Olasagasti ........... | C12Q 1/6869 435/6.16 |
| 2010/0084276 A1 * | 4/2010 | Lindsay ............... | C12Q 1/6869 205/93 |
| 2010/0184020 A1 | 7/2010 | Beer | |
| 2010/0267013 A1 | 10/2010 | Su et al. | |
| 2011/0003343 A1 | 1/2011 | Nikiforov et al. | |
| 2011/0120868 A1 * | 5/2011 | Lindsay ................. | B82Y 15/00 204/452 |
| 2012/0214171 A1 | 8/2012 | Kotseroglou | |
| 2013/0078622 A1 * | 3/2013 | Collins .................. | G01N 27/26 435/6.1 |
| 2013/0146457 A1 * | 6/2013 | Gundlach ........ | G01N 33/48721 204/451 |
| 2013/0165328 A1 * | 6/2013 | Previte ................. | C12Q 1/6874 506/2 |
| 2014/0051068 A1 * | 2/2014 | Cherf ................... | C12Q 1/6869 435/6.1 |
| 2014/0147833 A1 * | 5/2014 | Astier .................. | C12Q 1/6869 435/5 |
| 2016/0011169 A1 * | 1/2016 | Turner ................. | C12Q 1/6874 204/452 |

FOREIGN PATENT DOCUMENTS

| | | |
|---|---|---|
| WO | WO 2012/083249 | 6/2012 |
| WO | WO 2012/164270 | 12/2012 |
| WO | WO 2013/014451 | 1/2013 |

OTHER PUBLICATIONS

Branton et al. (The potential and challenges of nanopore sequencing, Nature Biotechnology 26, 1146-1153 (2008), Published online: Oct. 9, 2008).*
Sadki et al. (Embedding a carbon nanotube across the diameter of a solid state nanopore, J. Vac. Sci. Technol. B 29, 053001 (Sep. 1, 2011)).*
Blow (DNA sequencing: generation next-next, Nature Methods—5, 267-274 (Mar. 2008)).*
International Search Report and Written Opinion in International Application No. PCT/US2014/17419, mailed Aug. 5, 2014, 17 pages.
International Preliminary Report on Patentability in International Application No. PCT/US2014/017419, dated Sep. 3, 2015, 13 pages.
Cherf et al., "Automated forward and reverse ratcheting of DNA in a nanopore at 5-angstrom precision," Nature Biotechnology, Feb. 2012, 30(4): 344-348.
European Search Report in European Application No. 14754640.2, dated Aug. 18, 2016, 8 pages.
Hague et al., "Solid-state and biological nanopore for real-time sensing of single chemical and sequencing of DNA," Nano Today, Feb. 2013, 8(1): 56-74.
Lieberman et al., "Processive Replication of Single DNA Molecules in a Nanopore Catalyzed by phi29 DNA Polymerase," Journal of the American Chemical Society, Dec. 2010, 132(50): 17961-17972.
Smeets et al., "Translocation of RecA-coated double-stranded DNA through solid-state nanopores," Nano Letters, Sep. 2009, 9(9): 3089-3096.

(Continued)

*Primary Examiner* — Aaron Priest
(74) *Attorney, Agent, or Firm* — Fish & Richardson P.C.

(57) ABSTRACT

Provided herein are nanostructure-based sequencing methods and systems. Such methods and systems include contacting an immobilized RNA polymerase with a double-stranded target nucleic acid molecule under sequencing conditions, where the sequencing conditions include the presence of four nucleoside triphosphates, where one of the nucleoside triphosphates is present in a rate-limiting amount; detecting the movement of the target nucleic acid molecule and/or one or more nascent strand(s) through, on or over a nanostructure; repeating the contacting and detecting steps a plurality of times; and determining the sequence of the target nucleic acid molecule based, sequentially, on the presence or absence of a change in the movement in the presence of the at least one nucleoside triphosphate.

16 Claims, 5 Drawing Sheets

(56) References Cited

OTHER PUBLICATIONS

Choi et al., "Single molecule recordings of lysozyme activity," Phys. Chem. Chem. Phys., Sep. 2013, 15(36): 14825-15244.
Olsen et al., "Electronic Measurements of Single-Molecule Processing by DNA Polymerase I (Klenow Fragment)," JACS, 2013, 135: 7855-7860.
Authorized Officer Leslie Ripaud, International Search Report and Written Opinion of the International Searching Authority, PCT/US2012/026339, mailed Jul. 4, 2012, 17 pages.
Abbondanzieri et al., "Direct observation of base-pair stepping by RNA polymerase," Nature, 2005, 438:460-465.
Akeson et al., "Microsecond Time-Scale Discrimination Among Polycytidylic Acid, Polyadenylic Acid, and Polyuridylic Acid as Homopolymers or as Segments Within Single RNA Molecules," Biophys. J., 1999, 77:3227-3233.
Braslaysky et al., "Sequence information can be obtained from single DNA molecules," PNAS USA, 2003, 100:3960-3964.
Capitanio et al., "Exploring molecular motors and switches at the single-molecule level," Microsc Res Tech., Nov. 2004, 65(4-5):194-204.
Davenport et al., "Single-molecule study of transcriptional pausing and arrest by *E.coli* RNA polymerase," Science, 2000, 287:2497-2500.
Deniz et al., "Single-molecule biophysics: at the interface of biology, physics and chemistry," J R Soc Interface, Jan. 6, 2008, 5(18):15-45.
Gosse et al., "Magnetic Tweezers: Micromanipulation and Force Measurement at the Molecular Level," Biophys. J., 2002, 82:3314-3329.
Greenleaf et al., "High-resolution single-molecule optical trapping measurements of transcription with basepair accuracy: instrumentation and methods," Proceedings of SPIE, Jan. 1, 2007, 664406-664406-8.
Greenleaf et al., "Passive All-Optical Force Clamp for High-Resolution LaserTrapping," Phys. Rev. Lett., 2005, 95(20):208102, 8 pages.
Han et al., "CMOS Integrated DNA Microarray Based on GMR Sensors," Electron Devices Meeting, 2006, IEDM '06 International, 4 pages.
Harada et al., "Direct observation of DNA rotation during transcription by *Escherichia coli* RNA polymerase," Nature, 2001, 409:113-115.
He et al., "Rapid mutagenesis and purification of phage RNA polymerases," J. Protein Expression Purif., 1997, 9:142-51.
He et al., "Thermophoretic manipulation of DNA translocation through nanopores," ACS Nano, 2013, 7:538-46.
Herbert et al., "Sequence-Resolved Detection of Pausing by Single RNA Polymerase Molecules," Cell, 2006, 125:1083-1094.
Kasas et al., "*Escherichia coli* RNA Polymerase Activity Observed Using Atomic Force Microscopy," Biochem., 1997, 36:461-468.
Keefe et al., "One-step purification of recombinant proteins using a nanomolar-affinity streptavidin-binding peptide, the SBP-Tag," J. Protein Expression Purif., 2001, 23:440-46.
Lipfert et al., "A method to track rotational motion for use in single-molecule biophysics," Rev. Sci. Instrum., 2011, 82:103707.
Manrao et al., "Reading DNA at single-nucleotide resolution with a mutant MspA nanopore and phi29 DNA polymerase," Nat. Biotech., 2012, 30:349-53.
Noji et al., "Direct observation of the rotation of F1-ATPase," Nature, 1997, 386:299-302.
Paik et al., "End-functionalization of poly(3-hydroxybutyrate)via genetic engineering for solid surface modification," Chem. Commun. (Camb), 2005, 15:1956-8.
Pomerantz et al., "A Tightly Regulated Molecular Motor Based upon T7 RNA Polymerase," Nano Letter, 2005, 5:1698-1703.
Ribeck & Saleh, "Multiplexed single-molecule measurements with magnetic tweezers," Rev. Sci. Instrum., 2008, 79:094301.
Rong et al., "Template strand switching by T7 RNA polymerase," J. Biol. Chem., 1998, 273(17):10253-60.
Rosenberg et al., "Rotational motions of macro-molecules by single-molecule fluorescence microscopy," Acc Chem Res., Jul. 2005, 38(7):583-593.
Sanger et al., "DNA sequencing with chain-terminating inhibitors," PNAS USA, 1977, 74:5463-5467.
Shaevitz et al., "Backtracking by single RNA polymerase molecules observed at near-base-pair resolution," Nature, 2003, 426:684-687.
Shundrovsky et al., "A Single-Molecule Technique to Study Sequence-Dependent Transcription Pausing," Biophys. J., 2004, 87:3945-3953.
Smeets et al., "Salt dependence of ion transport and DNA translocation through solid-state nanopores," Nano Lett., 2006, 6:89-95.
Thomen et al., "Unraveling the mechanism of RNA-polymerase forward motion by using mechanical force," Phys. Rev. Lett., 2005, 94:128102.
Tsutsui et al., "Transverse electric field dragging of DNA in a nanochannel," Sci. Rep., 2012, 2:394, 7 pages.
Zlatanova et al., "Single-molecule approaches reveal the idiosyncrasies of RNA polymerases," Structure, Jun. 1, 2006, 14(6):953-966.

* cited by examiner

SEQUENCE LISTING

```
<160> NUMBER OF SEQ ID NOS: 4

<210> SEQ ID NO 1
<211> LENGTH: 66
<212> TYPE: DNA
<213> ORGANISM: Artificial Sequence
<220> FEATURE:
<223> OTHER INFORMATION: oligonucleotide

<400> SEQUENCE: 1
gcagtaatac gactcactat agggagaggg agggatggag cctttaagga ggtcaaatgg    60
```

```
ctaacg                                                                    66

<210> SEQ ID NO 2
<211> LENGTH: 34
<212> TYPE: DNA
<213> ORGANISM: Artificial Sequence
<220> FEATURE:
<223> OTHER INFORMATION: oligonucleotide

<400> SEQUENCE: 2
ggcatctaga tgcatccta tgcagtccta atgc                                      34

<210> SEQ ID NO 3
<211> LENGTH: 34
<212> TYPE: DNA
<213> ORGANISM: Artificial Sequence
<220> FEATURE:
<223> OTHER INFORMATION: oligonucleotide

<400> SEQUENCE: 3
ggcagctagc taaacatggc gctgtacgtt tcgc                                     34

<210> SEQ ID NO 4
<211> LENGTH: 24
<212> TYPE: DNA
<213> ORGANISM: Artificial Sequence
<220> FEATURE:
<223> OTHER INFORMATION: oligonucleotide

<400> SEQUENCE: 4
agcctttcgg atcgaacacg atga                                                24
```

METHODS AND COMPOSITIONS FOR NANOSTRUCTURE-BASED NUCLEIC ACID SEQUENCING

CROSS REFERENCE TO RELATED APPLICATIONS

This application claims benefit under 35 U.S.C. §119(e) to U.S. Application No. 61/766,925, filed on Feb. 20, 2013.

TECHNICAL FIELD

This disclosure generally relates to nucleic acid sequencing systems and methods and compositions that can be used in such systems and methods.

BACKGROUND

Nanostructure DNA sequencing is one method of DNA sequencing that can lead to cost-effective, long read and accurate whole human genome sequencing and efficient bacterial genome sequencing and other sequencing applications. The present disclosure provides numerous improvements over existing nanostructure sequencing technology and addresses many of the limitations that have restricted the use of nanostructure-based sequencing methods in, for example, clinical applications and high-throughput environments.

SUMMARY

Nanostructure based sequencing relies upon the polymerase being immobilized relative to a solid surface in the vicinity of a nanostructure. As a consequence of base incorporation and elongation by the polymerase, the nucleic acid translocates within the polymerase enzyme and, as a consequence, through, on, or over the nanostructure. A change in the electronic signal across the nanostructure is observed as a result of the enzyme-dependent translocation. The methods of sequencing described herein encompass two approaches. The first approach is a base-by-base sequencing, where a known base addition leads to single base polymerization and translocation (i.e., movement) through, on, or over the nanostructure. In a second approach, all four nucleotides are present with one of the nucleotides present in a rate-limiting amount. During incorporation of three of the four nucleotides and subsequent elongation by the polymerase, movement of the nucleic acid through, on, or over the nanostructure occurs at the normal rate of the enzyme. However, at the positions within the nucleic acid that correspond to the rate-limiting nucleotide, elongation/translocation and, hence, movement through, on, or over the nanostructure, slows down or pauses. Iterative reactions with each nucleotides at a rate-limiting concentration allows for bioinformatically assembling the complete sequencing.

In one aspect, a method of determining the sequence of a target nucleic acid molecule is provided. Such a method typically includes contacting a polymerase with a target nucleic acid molecule under sequencing conditions, wherein sequencing conditions comprise the presence of at least one nucleoside triphosphate, wherein the polymerase is immobilized on a solid substrate; detecting the movement of the target nucleic acid molecule and/or one or more nascent strand(s) through, on, or over a nanostructure; repeating the contacting and detecting steps a plurality of times; and determining the sequence of the target nucleic acid molecule based, sequentially, on the presence or absence of a change in the movement in the presence of the at least one nucleoside triphosphate. In some embodiments, the sequencing conditions comprise the presence of a single nucleoside triphosphate. In some embodiments, the sequencing conditions comprise the presence of four nucleoside triphosphates, where a first nucleoside triphosphate of the four nucleoside triphosphates is present in a rate-limiting amount.

Representative solid substrates are glass. In one embodiment, the polymerase is a RNA polymerase. Representative RNA polymerases include, for example, bacteriophage RNA polymerases (e.g., T7 RNA polymerase and a T3 RNA polymerase) and bacterial RNA polymerase (e.g., an *E. coli* RNA polymerase). In one embodiment, the polymerase is a DNA polymerase. Representative DNA polymerases include, for example, phi29 DNA polymerase, T7 DNA polymerase, *Bacillus subtilis* DNA polymerase, and Taq DNA polymerase. In some embodiments, the polymerase is immobilized on the solid surface via a His-tag or via one or more biotin-streptavidin bonds.

In some embodiments, the target nucleic acid molecule is eukaryotic. The target nucleic acid molecule can be double-stranded or single-stranded. In some embodiments, the target nucleic acid molecule is included within or as a part of a biological sample. In some embodiments, the target nucleic acid molecule includes a polymerase promoter sequence. In some embodiments, the target nucleic acid molecule further includes a magnetic tag.

Representative nanostructures include, for example, biological nanostructures, solid state nanostructures, or combinations thereof. In some embodiments, the detecting step includes measuring a change in electric current through, on, or over the nanostructure and/or measuring a change in ionic conduction of the nanostructure. The detecting step can further include capturing movement on a CMOS based manufactured nanostructure and electronics. In some embodiments, the method further includes applying a directional force on the target nucleic acid molecules. In some embodiments, the directional force is produced with a magnet. In some embodiments, the directional force is produced with flow or pressure.

In another aspect, a method of determining the sequence of a target nucleic acid molecule is provided. Such a method typically includes providing a solid substrate onto which polymerase is immobilized; contacting the polymerase with the target nucleic acid molecule under first sequencing conditions, wherein the first sequencing conditions comprise the presence of four nucleoside triphosphates, where a first nucleoside triphosphate of the four nucleoside triphosphates is present in a rate-limiting amount; detecting the movement of the target nucleic acid molecule and/or one or more nascent strand(s) through, on, or over a nanostructure under the first sequencing conditions; and determining positional information of the first nucleoside triphosphate along the target nucleic acid molecule based on a change in the movement. Such a method can further include providing a solid substrate onto which polymerase is immobilized; contacting the polymerase with the target nucleic acid molecule under second sequencing conditions, wherein the second sequencing conditions comprise the presence of four nucleoside triphosphates, where a second nucleoside triphosphate of the four nucleoside triphosphates is present in a rate-limiting amount; detecting the movement of the target nucleic acid molecule and/or one or more nascent strand(s) through, on, or over a nanostructure under the second sequencing conditions; and determining positional information of the second nucleoside triphosphate along the target nucleic acid molecule based on a change in the movement. In some embodiments, the contacting and detecting steps under the second sequencing conditions are performed simultaneously with the contacting and detecting steps under the first sequencing conditions. In some embodiments, the contacting and detecting steps under the second sequencing conditions are performed sequentially before or after the contacting and detecting steps under the first sequencing conditions. Such a method can further include providing a solid substrate onto which polymerase is immobilized; contacting the polymerase with the target nucleic acid molecule under third sequencing conditions, wherein the third sequencing conditions comprise the presence of four nucleoside triphosphates, where a third nucleoside triphosphate of the four nucleoside triphosphates is present in a rate-limiting amount; detecting the movement of the target nucleic acid molecule and/or one or more nascent strand(s) through, on, or over a nanostructure under the third sequencing conditions; and determining positional information of the third nucleoside triphosphate along the target nucleic acid molecule based on a change in the movement. Such a method typically includes determining the sequence of the target nucleic acid molecule from the positional information for the first, second and third nucleoside triphosphates within the target nucleic acid molecule. Such a method can further include providing a solid substrate onto which polymerase is immobilized; contacting the polymerase with the target nucleic acid molecule under fourth sequencing conditions, wherein the fourth sequencing conditions comprise the presence of four nucleoside triphosphates, where a fourth nucleoside triphosphate of the four nucleoside triphosphates is present in a rate-limiting amount; detecting the movement of the target nucleic acid molecule and/or one or more nascent strand(s) under the fourth sequencing conditions; and determining positional information of the fourth nucleoside triphosphate along the target nucleic acid molecule based on a change in the movement.

In still another aspect, a method of determining the sequence of a target nucleic acid molecule is provided. Such a method typically includes providing a solid substrate onto which one or more polymerases are immobilized; contacting the one or more polymerases with the target nucleic acid molecule under first sequencing conditions, wherein the first sequencing conditions comprise the presence of a first of four nucleoside triphosphates; and detecting, under the first sequencing conditions, whether a change in the movement of the target nucleic acid molecule and/or one or more nascent strand(s) through, on, or over a nanostructure occurs. If a change in the movement occurs, the method further includes repeating the contacting step and subsequent steps under the first sequencing conditions, but if a change in the movement does not occur, the method further includes repeating the contacting step and subsequent steps under second sequencing conditions, wherein the second sequencing conditions comprise the presence of a second of four nucleoside triphosphates. If a change in the movement occurs, the method further includes repeating the contacting step and subsequent steps under the first sequencing conditions, but if a change in the movement does not occur, the method further includes repeating the contacting step and subsequent steps under third sequencing conditions, wherein the third sequencing conditions comprise the presence of a third of four nucleoside triphosphates. Lastly, the method includes determining the sequence of the target nucleic acid molecule based, sequentially, on the occurrence of a change in the movement under the first, second, or third sequencing conditions.

In yet another aspect, an article of manufacture is provided. Such an article of manufacture generally includes a solid substrate onto which a plurality of polymerases are immobilized, wherein the solid substrate comprises a plurality of nanostructures. In some embodiments, the solid substrate is coated with copper and PEG. In some embodiments, the solid substrate is coated with nickel and PEG. In some embodiments, the solid substrate is coated with Ni-NTA. In some embodiments, the solid substrate is a CMOS or CCD. In some embodiments, the plurality of polymerases includes RNA polymerases, DNA polymerases, or a combination thereof. Such an article of manufacture further can include polymerase promoter sequences, biotinylated nucleic acid tether sequences, and/or one or more nucleoside triphosphates. In some embodiments, such an article of manufacture can further include instructions for identifying movement of the target nucleic acid molecule and/or one or more nascent strand(s) through, on, or over a nanostructure; compiling a sequence of a target nucleic acid molecule based on the movement and the presence of a nucleoside triphosphate; and/or applying a directional force. In some embodiments, the instructions are provided in electronic form.

In another aspect, an apparatus for single-base sequencing of target nucleic acid molecules is provided. Such an apparatus typically includes a Sequencing Module. The Sequencing Module generally includes a receptacle for receiving a solid substrate, wherein the solid substrate comprises a plurality of polymerases immobilized thereon and a plurality of nanostructures; a source for providing directional force, wherein the directional force is sufficient and in a direction such that tension is applied to target nucleic acid molecules being polymerized by the plurality of polymerases immobilized on the solid surface; and means for determining changes in an electric current and/or an ionic conduction of the nanostructures. In some embodiments, the apparatus further can include a computer processor. In some embodiments, the apparatus can further include microfluidics for containing and transporting reagents and buffers involved in sequencing nucleic acids. Representative reagents can include nucleoside triphosphates. Representative buffers can include a wash buffer, an enzyme-binding buffer, and/or a sequencing buffer. In some embodiments, the source for providing directional force includes a magnet and/or flow of liquid.

Such an apparatus also can include a Sample Preparation Module, which can include a receptacle for receiving a biological sample; and fluidics for containing and transporting reagents and buffers involved in isolating and preparing nucleic acids for sequencing. Representative reagents include cell lysis reagents and cleavage enzymes. Representative buffers include lysis buffer and wash buffer.

Such an apparatus also can include a Template Finishing Module, which can include fluidics for containing and transporting reagents and buffers involved in attaching polymerase promoter sequences to nucleic acid molecules. Representative reagents include a ligase enzyme, a molecular motor-binding sequence, and a tether. Representative buffers include ligase buffer, magnetic tag-binding buffer, and enzyme-binding buffer.

In another aspect, a method of determining the sequence of a target nucleic acid molecule based upon data obtained during polymerization of the target nucleic acid molecule is provided. Such a method includes receiving a first datum for a first position of the target nucleic acid molecule, wherein the first datum indicates the presence or absence of movement of a target nucleic acid molecule and/or one or more nascent strand(s) through, on, or over a nanostructure and/or the rate of movement of the strand(s) through, on, or over the nanostructure; receiving a second datum for the first position of the target nucleic acid molecule, wherein the second datum indicates the presence and/or amount of one or more nucleoside triphosphates available during polymerization; receiving another first datum and another second datum for a second position of the target nucleic acid molecule; receiving yet another first datum and yet another second datum for a third position of the target nucleic acid molecule; repeating the receiving steps of the first datum and the second datum for a fourth and subsequent positions of the target nucleic acid molecule; and determining a sequence of the target nucleic acid molecule based on the first datum and second datum received for each position. In some embodiments, the first datum and the second datum is recorded as a nucleotide at an indicated position.

Unless otherwise defined, all technical and scientific terms used herein have the same meaning as commonly understood by one of ordinary skill in the art to which the systems, methods and compositions of matter belong. Although systems, methods and materials similar or equivalent to those described herein can be used in the practice or testing of the systems, methods and compositions of matter, suitable systems, methods and materials are described below. In addition, the systems, materials, methods, and examples are illustrative only and not intended to be limiting. Any publications, patent applications, patents, and other references mentioned below are incorporated by reference in their entirety.

DETAILED DESCRIPTION

Figure 1:
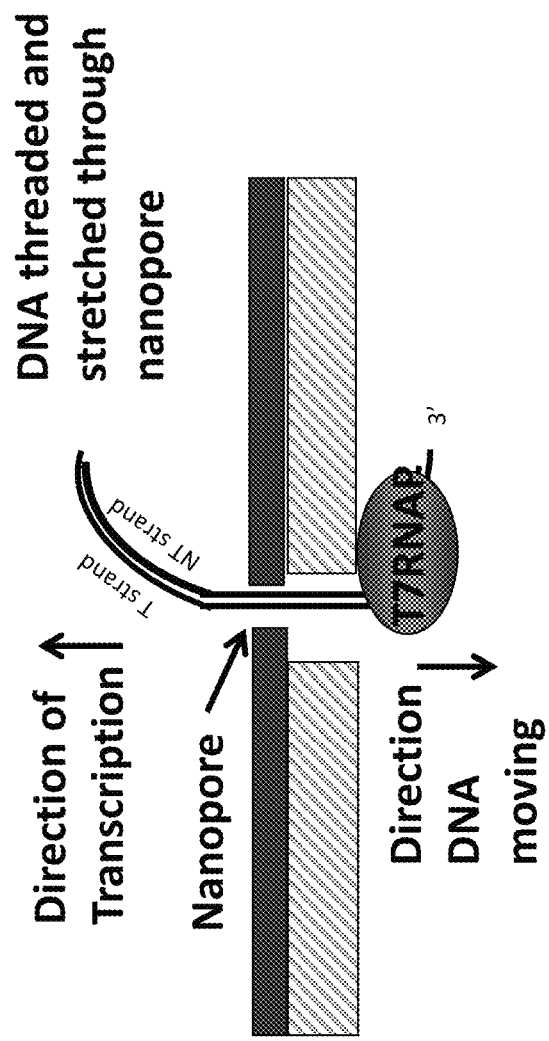
FIG. 1 shows an embodiment of a single-molecule nanostructure-based sequencing complex. The enzyme, in this embodiment, T7 RNA polymerase, is attached to a functionalized surface on one side of, in this embodiment, a nanopore via His-tag or other methods, and the nucleic acid is threaded through the nanostructure. Sequencing as described herein is performed, which translocates the nucleic acid through the enzyme and through, in this embodiment, the nanopore.

The present disclosure describes a single molecule nanostructure-based sequencing system in which many of the constraints of existing single molecule sequencing system are relaxed, including complexity, cost, scalability and, ultimately, longer read lengths, higher throughput and enhanced accuracy. The real time, single molecule nanostructure-based sequencing method and system described herein can sequence thousands of nucleotides in a very short time with high accuracy due to the use of highly processive enzymes and nanostructure technology.

The advantages of the present nanostructure-based sequencing systems are numerous. For example, double-stranded nucleic acid or single-stranded nucleic acid can be used as the template, which minimizes and reduces the requirements for sample preparation. In addition, labeled nucleotides are not required, since detection is performed using translocation through, on, or over nanostructures, which also significantly reduces the cost. Also, wild type polymerase enzymes can be used; no special modifications to the enzyme are necessary, and the surface chemistry and enzyme immobilization technologies also are routine. The present nanostructure-based sequencing systems and methods are suitable for homopolymeric sequences, since translocation through, on, or over the nanostructure is detectable for each nucleotide. Thus, the movement is cumulative over multiple nucleotides, even when the nucleotides are the same. The present nanostructure-based sequencing systems and methods also are readily adaptable for high throughput sequencing since multiple nanostructures can be used on a single solid surface. Notably, the polymerase enzymes regulate the rate of translocation through, on, or over the nanostructure, which is a significant problem for current nanostructure-based sequencing systems and methods but, in the present systems and methods, can ultimately lead to even higher throughput.

Overview of Nanostructure-Based Sequencing

Nanostructure-based sequencing relies upon elongation and translocation of the target nucleic acid molecules by polymerase enzymes, which also causes translocation of the target nucleic acid molecules through, on, or over the nanostructures. In one embodiment, a polymerase is immobilized on a solid surface, and a target nucleic acid is attached at one end to the polymerase while the other end is threaded through, on, or over a nanostructure. Solid state nanostructures such as nanopores or nanotubes typically have a larger opening than biological nanostructures and, thus, can accommodate double-stranded nucleic acids. The nanostructure can detect asymmetric ionic responses during movement of the nucleic acid through, on, or over the nanostructure, which signals elongation and translocation of a nucleotide base.

In one embodiment, a base-by-base (or synchronous) sequencing reaction can be performed, in which a single nucleotide is present. Reactions can then be performed that iterate between the other nucleotides. In another embodiment, an asynchronous sequencing reaction can be performed, in which all four nucleotides are present but one of the four nucleotides is provided in a rate-limiting amount. This results in a pause by the polymerase when trying to incorporate the rate-limiting nucleotide, and the change in the translocation (i.e., movement) of the nucleic acid through, on, or over the nanostructure indicates the presence of the rate-limiting nucleotide at that position. The entire sequence then can be compiled bioinformatically using, for example, four different reactions in which one of the four bases is provided in a rate-limiting amount. The different types of sequencing reactions are discussed in more detail below.

Figure 2:
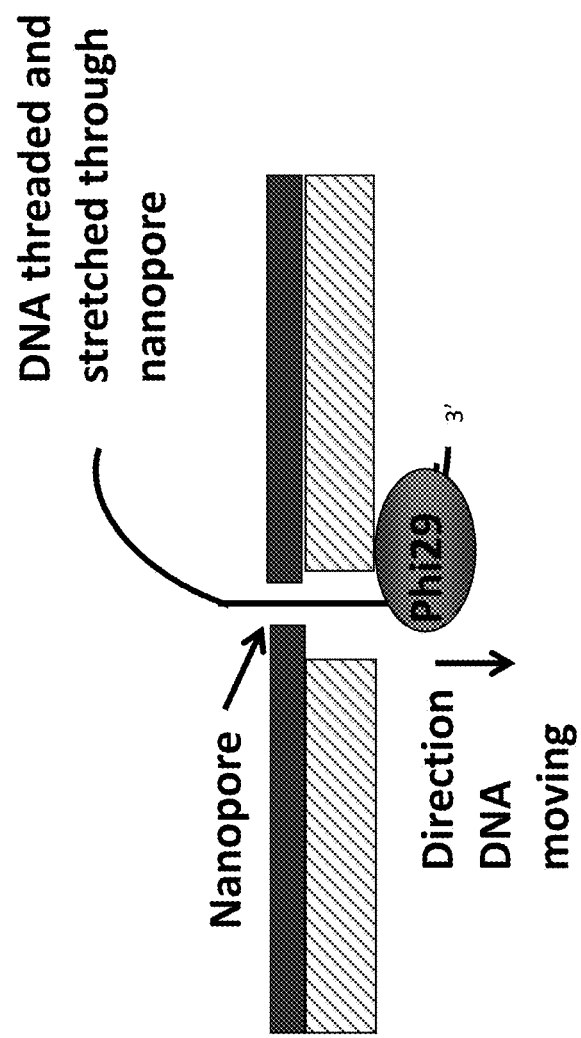
FIG. 2 shows an embodiment of a single-molecule nanostructure-based sequencing complex that utilizes, in this embodiment, a DNA polymerase. The enzyme is attached to a functionalized solid surface on one side of, in this embodiment, a nanopore. The nucleic acid is threaded and stretched through the nanostructure. Sequencing is performed as described herein and the nucleic acid is translocated through, in this embodiment, the nanopore.

FIGS. 1 and 2 show a single-molecule nanostructure-based sequencing complex as described herein. FIG. 1 is an embodiment of a nanostructure-based sequencing complex that includes a T7 RNA polymerase (e.g., T7 RNAP), while FIG. 2 is an embodiment of a nanostructure-based sequencing complex that includes a DNA polymerase (e.g., Phi29). As described in more detail below, the polymerase enzyme can be immobilized on a functionalized surface in the vicinity of a nanostructure via a His-tag or other method. The target nucleic acid molecule can be complexed with the enzyme prior to the enzyme being immobilized on the solid substrate, or the target nucleic acid molecule can be complexed with the enzyme after the enzyme has been immobilized on the solid surface. The target nucleic acid molecule is threaded or fed through, on, or over the nanostructure, and sequencing is initiated in either a base-by base fashion or an asynchronous fashion as described herein. During each step of base incorporation by the polymerase enzyme, the nucleic acid is translocated through, on, or over the nanostructure, which is detected. In the nanostructure-based sequence methods described herein, the nanostructure detects movement by the nucleic acid due to base incorporation by the polymerase; the nanostructure is not used to distinguish the nucleotide base.

Each of the features of a nanostructure-based sequencing reaction is discussed in more detail below.

Solid Surface

For the nanostructure-based sequencing methods described herein, an enzyme (RNA polymerase or DNA polymerase) is immobilized on a solid surface. In some embodiments described herein, a solid surface is made from a silica-based glass (e.g., borosilicate glass, fused silica, or quartz). In other embodiments, Aluminum Oxide, silicon, Graphene or other surfaces used in the semiconductor art as substrates or layers on substrates. However, other materials (e.g., polypropylene, polystyrene, silicon, silicon nitride, and other polymers or composites thereof) also can be used provided they are suitable for use in the sequencing described herein.

Before immobilizing one or more polymerases into a solid surface, the solid surface generally is modified (e.g., functionalized) to receive and bind the polymerase. Methods of functionalizing solid surfaces for immobilizing enzymes are known in the art. In some embodiments, the solid surface can be functionalized with copper or nickel, while in some embodiments, the solid surface can be functionalized with Ni-NTA (see, for example, Paik et al., 2005, *Chem. Commun. (Camb)*, 15:1956-8) or Cu-NTA. Alternatively, metals such as cobalt or the like can be used to modify a solid surface for immobilization.

Prior to modifying a solid surface, the solid surface can be treated with, for example, PEG moieties. Such strategies can be used to regulate the density of polymerases on a solid surface, and also can be used to generate a pattern of polymerases on the solid surface, such as a uniform, a semi-ordered or a random array of polymerases. The PEG environment results in minimal interactions between the enzyme and the surface (except for the binding tag on the N- or C-terminus), and ultimately results in minimal disturbance to the native conformation of the immobilized enzyme. In addition, surface passivation methods are known in the art and can include, for example, treating the solid surface with bovine serum albumin (BSA).

The solid surface can be functionalized in an array format so that a preferred location of the enzyme attachment with respect to the nanostructure can be achieved. This location, in some embodiments, can be close, or right next to, or surrounding the nanostructure. In some instances, the enzyme may partially overlap the nanostructure or it may be attached in a channel that allows for fluid communication between the nanostructure and one or more reagents or buffers. Methods for arranging enzymes in particular locations are known in the art. Positioning the enzymes with respect to the nanostructures also is feasible using methods known in the art (e.g., TEM, SEM, AFM). For coarse location readout, high resolution optical imaging can be adequate, particularly when the functional area can be tagged with fluorescence moieties that then can either be cleaved to make room for the enzymes or left in place while enzymes are positioned nearby.

Polymerase Enzymes

The nanostructure-based sequencing methods described herein can utilize any type of polymerase enzyme. Polymerases (EC 2.7.7.6; EC 2.7.7.7; EC 2.7.7.19; EC 2.7.7.48; or EC 2.7.7.49) synthesize one or two new strands of DNA or RNA from single-stranded or double-stranded template DNA or RNA. Suitable polymerases include, for example, DNA polymerases and RNA polymerases.

A representative DNA polymerase is phi29. Other DNA polymerases are well known in the art, and many that have been used in single molecule sequencing platforms that rely upon fluorescence also would be suitable for use in the present nanostructure-based sequencing methods. Representative DNA polymerases include, without limitation, T7 DNA polymerase, *Bacillus subtilis* DNA polymerase, and Taq DNA polymerase.

Any number of RNA polymerase enzymes can be used in the present methods. For example, multi-subunit RNA polymerases (e.g., *E. coli* or other prokaryotic RNA polymerase or one of the eukaryotic RNA polymerases) can be used in the sequencing methods described herein. However, it would be understood that the small, single-subunit RNA polymerases such as those from bacteriophage are particularly suitable. Single subunit RNA polymerases or the genes encoding such enzymes can be obtained from the T3, T7, SP6, or K11 bacteriophages.

The bacteriophage RNA polymerases are very processive and accurate compared to many of the multi-subunit RNA polymerases, and often produce fewer deletion-insertion errors. Additionally, RNA polymerases from bacteriophage are significantly less prone to back-tracking compared to multi-subunit counterparts such as the RNA polymerase from *E. coli*. RNA polymerase from several different bacteriophages has been described. Simply by way of example, the T7 RNA polymerase is made up of a single polypeptide having a molecular weight of 99 kDa, and the cloning and expression of the gene encoding T7 RNA polymerase is described in U.S. Pat. No. 5,693,489. The structure of T7 RNA polymerase has been resolved to a level of 3.3 Angstroms, with four different crystal structures having been solved: T7 RNA polymerase alone (uncomplexed), T7 RNA polymerase bound to a nucleic acid promoter, the entire initiation complex (T7 RNA polymerase bound to a nucleic acid promoter and one or more transcription factors), and T7 RNA polymerase bound by an inhibitor.

The density and/or distribution of polymerases on a solid surface can be controlled or manipulated, for example, to optimize the particular sequencing reactions being performed. As is known in the art, an array of biological molecules can be generated in a pattern. For example, an array of biological molecules can be randomly distributed on the solid surface, uniformly distributed or distributed in an ordered or semi-ordered fashion using, for example, the functionalization described herein. In some embodiments, a solid surface can have greater than 100 polymerases, or greater than 1000 polymerases (e.g., greater than 10,000 polymerases, greater than 100,000 polymerases, or greater than 1,000,000 polymerases) immobilized thereon. In some embodiments, a solid surface can have at least one polymerase immobilized per ~5 $\mu m^2$ (e.g., at least one polymerase immobilized per ~2.5 $\mu m^2$, ~1 $\mu m^2$, ~0.5 $\mu m^2$, or ~0.1 $\mu m^2$). It would be understood that the density of polymerases on a solid surface may depend, at least in part, upon the size of the target nucleic acid molecules being sequenced as well as the number, location and size of the nanostructures. As indicated herein, the polymerase enzymes can be positioned close to, right next to, overlapping with, or surrounding the nanostructure.

Polymerase enzymes can be immobilized on a solid surface using any number of known means. For example, in some embodiments, the polymerase contains a His-tag (e.g., His tags having 4 His residues, 6 His residues, or 10 His residues). In some embodiments, the polymerase is immobilized on the solid surface via one or more biotin-streptavidin bonds. A His-tag, a biotin-streptavidin binding pair or other suitable means can be used provided it is compatible with the surface chemistry (e.g., functionalization) discussed above. A polymerase can be immobilized to a solid surface in close proximity to a nanostructure or a polymerase can be immobilized to a solid surface at the same position as a nanostructure.

Target Nucleic Acid Molecules

Nucleic acid molecules for nanostructure-based sequencing can be obtained from virtually any source including eukaryotes, bacteria and archaea. Eukaryotic nucleic acids can be from humans or other mammals (e.g., primates, horses, cattle, dogs, cats, and rodents) or non-mammals (e.g., birds, reptiles (e.g., snakes, turtles, alligators, etc.) and fish), while prokaryotic nucleic acids can be from bacteria (e.g., pathogenic bacteria such as, without limitation, *Streptococcus, E. coli, Pseudomonas*, and *Salmonella*) or Archaea (e.g., Crenarchaeota, and Euryarchaeota).

Nucleic acid molecules for nanostructure-based sequencing can be contained within any number of biological samples. Representative biological samples include, without limitation, fluids (e.g., blood, urine, semen) and tissues (e.g., organ, skin, mucous membrane, and tumor).

As discussed herein, one of the advantages of the nanostructure-based sequencing methods described herein is that double-stranded or single-stranded nucleic acid can be used as the template. This reduces the need to manipulate the sample and the nucleic acid, which is a significant advantage, particularly when sequencing nucleic acids greater than 1 Kilobase (Kb; e.g., greater than 2 Kb, greater than 5 Kb, greater than 10 Kb, greater than 20 Kb, or greater than 50 Kb, or greater than 75 kb, or greater than 100 kb, or greater than 150 Kb) in length, since many methods used to obtain nucleic acids from biological samples result in undesired cleavage, shearing or breakage of the nucleic acids. Single-stranded nucleic acids (or samples containing single-stranded nucleic acids) can be used directly in the present methods or can be converted into a double-stranded nucleic acid. Methods of making double-stranded nucleic acids are well known in the art and will depend upon the nature of the single-stranded nucleic acid (e.g., DNA or RNA). Such methods typically include the use of well known DNA polymerases and/or Reverse Transcriptase enzymes. It would be understood that different enzymes utilize different templates (e.g., DNA or RNA, single-stranded or double-stranded), and that the choice of polymerases to be immobilized on the solid surface will depend, at least in part, upon the target nucleic acid being sequenced.

Sample preparation will be dependent upon the source, but typically will include nucleic acid isolation followed by promoter ligation. Nucleic acid templates used in the sequencing methods described herein do not require any special preparation and, thus, standard DNA isolation methods can be used. Also, a promoter sequence that is recognized by the particular polymerase must be ligated to the target nucleic acid molecules. Promoter sequences recognized by a number of polymerases, both DNA and RNA polymerases, are known in the art and are widely used. In addition, methods of ligating one nucleic acid molecule (e.g., a promoter sequence) to another nucleic acid molecule (e.g., a target nucleic acid molecule having an unknown sequence) are well known in the art and a number of ligase enzymes are commercially available.

In addition, isolated nucleic acids optionally can be fragmented and, if desired, particular sizes can be selected or fractionated. For example, isolated nucleic acids can be fragmented using ultrasonication and, if desired, size-selected using routine gel electrophoresis methodology. In addition, the target nucleic acids optionally can be circularized into, for example, a plasmid, so that sequencing can be performed on a circular target in a repetitive or recursive fashion.

Other moieties (e.g., tags) can be attached to target nucleic acid molecules using tethers. These moieties can be attached after the target nucleic acid molecules are threaded through, on, or over the nanostructures. Such moieties can be used, for example, to exert force on the target nucleic acid molecule (as discussed in more detail below), to fluoresce, to rotate with transcription, to indicate the location of the enzyme/target nucleic acid, or other functionalities that assist in deducing the location or movement of the target nucleic acid molecule through, on, or over the nanostructure or of the segments of target nucleic acid molecules that are outside or have exited the nanostructure area.

Tethers to attach moieties (e.g., tags) to target nucleic acid molecules are known in the art and include, without limitation, a chemical linkage (e.g., crosslinking, van der Walls or hydrogen bond) or a protein linkage (e.g., biotin-streptavidin binding pairs, digoxigenin and a recognizing antibody, hydrazine bonding or His-tagging). For example, in some embodiments, a moiety can be coated, at least partially, with streptavidin, while a biotinylated nucleic acid tether can be ligated to the target nucleic acid molecules. In some embodiments, a biotin-labeled nucleic acid (e.g., about 500 base pairs (bp)) can be ligated to one end of the target nucleic acid molecules. The target nucleic acid molecules having the biotin-labeled tether then can be combined with streptavidin-coated moieties. In one embodiment, a moiety as used herein can refer to a bead. There are a number of commercially available beads, including magnetic beads, that are coated or partially coated with various chemistries that can be used to tether the target nucleic acid molecules and/or bind a second moiety (e.g., Dynal, Invitrogen, Spherotech, Kisker Inc., Bangs Laboratories Inc.).

Tension on the Nucleic Acid Molecules

Tension on the target nucleic acid molecules becomes important with longer target nucleic acid molecules, as longer nucleic acid molecules can fold-up or collapse on themselves. Any type of abnormal helical structure of the target nucleic acid molecules could dampen or mask the movement through, on, or over the nanostructure and, therefore, the sequencing signal.

A directional force applied to the target nucleic acid molecules needs to be sufficient so as to avoid the folding or collapse of the target nucleic acid molecule discussed above, particularly when the end of the target nucleic acid molecule is thousands or hundreds of thousands of nucleotides away from the polymerase. However, the directional force applied to the target nucleic acid molecules can't be so strong (i.e., apply so much tension) such that elongation/translocation is impeded in any way or the backbone of the target nucleic acid molecule breaks. Such tension on the target nucleic acid molecules also can reduce the Brownian motion that can occur at the free end of a long target nucleic acid molecule or other noise effects (e.g., thermofluidic noise effects), thereby increasing the accuracy of detecting translocation (i.e., movement) through, on, or over the structure.

Figure 3:
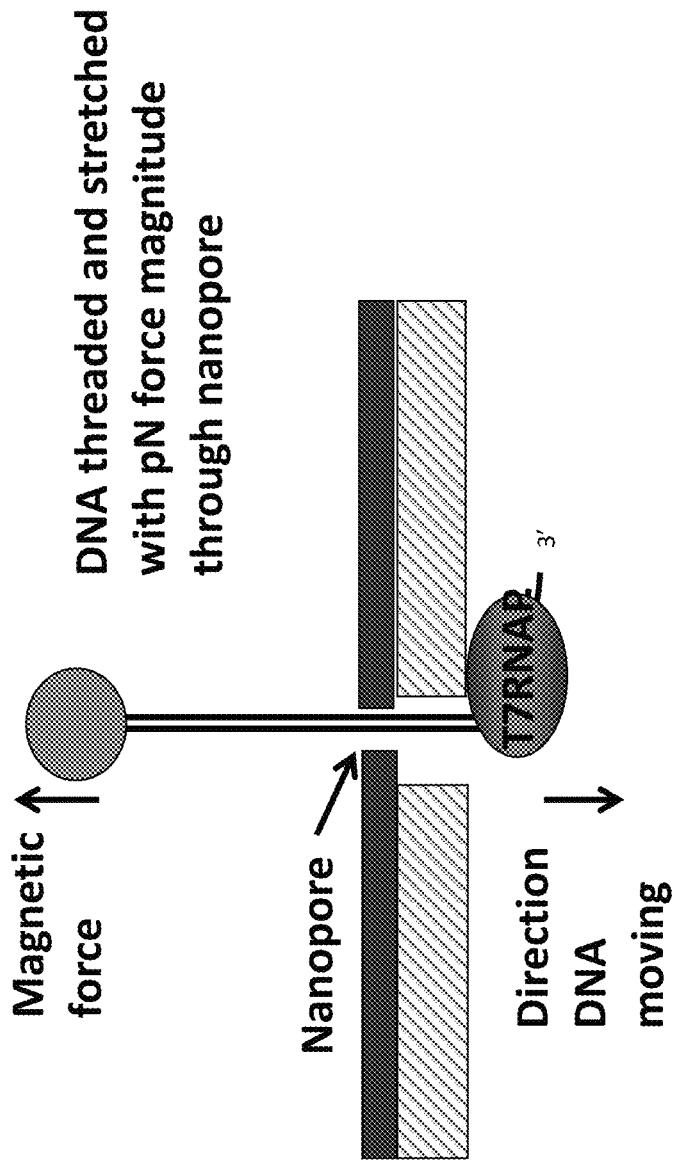
FIG. 3 shows an embodiment of a single-molecule nanostructure-based sequencing complex in which a magnetic bead and a magnetic force is used to stretch and apply tension to the nucleic acid. The enzyme, in this embodiment, T7 RNA polymerase, is attached to a functionalized solid surface near, in this embodiment, a nanopore. A magnetic bead is attached at or near the end of the nucleic acid and, using magnetic force, tension is applied and the nucleic acid is stretched. Sequencing is performed as described herein and the nucleic acid is translocated through in this embodiment, the nanopore.

In some embodiments, the tension source (or the source of the directional force) can be a magnet. In such cases, the target nucleic acid molecule can be labeled with a moiety that is magnetic (e.g., a magnetic tag). See, for example, FIG. 3. Magnetic tags (e.g., beads, rods, etc.) are well known in the art. For example, a magnetic force can be applied that provides a uniform spatial force in the direction of the z-axis at a magnitude of, for example, about 1 pN, to adequately stretch the target nucleic acid molecules and avoid any looping. At the same time, such magnets generate only a miniscule force in the direction of the x-axis. These features do not impede movement (i.e., elongation and translocation of the target nucleic acid molecule through the polymerase enzyme and through, on, or over the nanostructure), while stabilizing any Brownian motion of the free end(s) of the target nucleic acid molecule. In some embodiments, the tension source can be a result of a directional flow of, for example, liquid (e.g., water or buffer) or air.

The amount of tension applied to the target nucleic acid molecules can be calibrated using standard fluidic methodology and incorporated in data acquisition and analysis process or base calling algorithms. For example, such a calibration can include monitoring the Brownian motion of a nucleic acid molecule being read by a polymerase, which is immobilized on the surface, at various locations above the surface, at various angles relative to the plane of the surface, and/or in different flows or magnetic fields and on various ionic concentrations of the buffer around the enzyme.

In certain embodiment and using the same technology as described above, tension can be applied to one or both of the nascent strands.

Threading the Nanostructure

As discussed herein, a polymerase enzyme, before or after being complexed with the template nucleic acid, can be immobilized on a solid surface directly on or in close proximity to a nanostructure. Once the template nucleic acid and the nanostructure are near one another, the nucleic acid can be introduced or threaded into the nanostructure using any number of methods including, for example, diffusion or electrical currents. It would be understood by those skilled in the art that entropic forces can affect the ability of the sample to enter the nanostructure, and that the interrelationship between diffusion and entropy depends on parameters such as the length of the nucleic acid and the size of the nanostructure. See, for example, He et al. (2013, ACS Nano, 7:538-46) for guidance.

It is known in the art that different types of nanostructures (e.g., nanotubes, nanopores) have different sizes of openings. Simply by way of example, biological nanostructures can have an opening of about 1 nm, graphene nanostructures can have an opening of about 0.5 nm, and silicon nitride nanostructures have been made with openings as small as about 2 nm. Therefore, it would be appreciated that the type of nucleic acid and the type of polymerase can determine the particular nanostructure used in the nanostructure-based sequencing methods described herein. For example, double stranded nucleic acids are usually too large to fit within nanostructures having, for example, a 1 nm opening (e.g., a biological nanostructure); therefore, those nanostructures can be used to detect the translocation of a single-stranded nucleic acid (e.g., single-stranded DNA or single-stranded RNA). In addition, a nanostructure can detect translocation of any number of different nucleic acids within the complex. For example, in some instances, a nanostructure can detect translocation of the template strand (e.g., single- or double-stranded RNA or DNA) as it is advanced by the enzyme; in some instances, a nanostructure can detect translocation of the nascent strand(s) (e.g., single- or double-stranded RNA or DNA) as it is being produced by the enzyme. Further, it would be understood that translocation of the template strand can be detected by the nanostructure in front of the enzyme or after leaving the enzyme.

The nanostructure-based sequencing methods described herein are designed to efficiently bring together a nucleic acid and a nanostructure such that the likelihood that the nanostructure will capture the nucleic acid is increased.

Nanostructures and Nanostructure-Based Sequencing

Nanostructures are well known in the art and include, without limitation, nanopores, nanotubes, and nanowires. Nanostructures can be produced using biological materials (e.g., proteins, e.g., a pore-forming protein), synthetic or solid-state materials (e.g., silicon, graphene, silicon nitride, aluminum oxide), or combinations thereof. The principle behind nanostructures is based on monitoring the ionic current passing through, on, or over the nanostructure as a voltage is applied. The passage of molecules or, in the present case, the translocation movement of the nucleic acid molecule, causes interruptions of, or changes in, the current level. Those skilled in the art would appreciate that the ionic concentration of the buffer in which the nanostructure resides can determine whether increases or decreases in the current are observed (see, for example, Smeets et al., 2006, NanoLett., 6:89-95). Thus, in some embodiments, a low ionic concentration can be used; in some embodiments, a high ionic concentration can be used.

In the nanostructure-based sequencing methods described herein, the nanostructure can detect the movement of one or more of the nucleic acids involved in the reaction. For example, the nanostructure can detect the translocation (i.e., movement) of the template nucleic acid molecule, prior to entering the polymerase enzyme, after exiting the polymerase enzyme, or both. In addition, the nanostructure can detect the translocation (i.e., movement) of one or more of the nascent strand(s) produced by the polymerase. The particular configuration will depend, at least in part, on the particular polymerase (e.g., the preferred strandedness of the template, the direction of synthesis, the strandedness of the newly-produced nucleic acid).

The basis of existing nanostructure-based sequencing methods is translocation of the nucleic acid through, on or over a nanostructure (e.g., biologic or solid state or hybrid), which is sensitive to differences between each of the four bases in a specific fashion, e.g. a specific calibration for each base. One significant hurdle to existing nanostructure-based sequencing methods is the differential sensitivity of the structure to each base. Currently, only biological pores have been shown to have adequate sensitivity and discrimination for distinguishing among the bases. Even with biological pores, however, software algorithms are used since the data is often ambiguous (e.g., identifying more than one base in the nanostructure at a single position). Therefore, existing nanostructure-based sequencing methods lack sufficient discrimination ability between the different bases.

Another limitation of existing nanostructure-based sequencing methods that contributes to low accuracy is that translocation occurs too fast. In these instances, the base does not remain in the vicinity of the nanostructure long enough to be discriminated based on its averaged signal signature with respect to the other three bases. In some cases, to counteract this, a molecular motor has been introduced in order to slow down translocation and allow the accurate detection of the electronic signal induced by each base within the nanostructure. However, even in instances in which the molecular motor is a polymerase (see, for example, Manrao et al., 2012, Nat. Biotech., 30:349-53), the base discrimination still occur within the nanostructure.

Another limitation of existing nanostructure-based sequencing technology is with the sample preparation. Nanostructure-based sequencing techniques can produce very long read lengths (e.g., 50 kb or greater), but prefer single-stranded nucleic acids to achieve the greatest sensitivity. However, long single-stranded nucleic acids can be difficult to produce. Double-stranded nucleic acids are more stable and more easily prepared. However, because biological nanostructures are small, double-stranded nucleic acids must be converted to single-stranded nucleic acids using additional methods and enzymes before being sequenced in nanostructure-based sequencing systems that utilize biological nanostructures. On the other hand, while solid-state nanostructures are larger and can accommodate double-stranded nucleic acids, the accuracy of reading two nucleotides (i.e., one on each strand) across a larger structure is significantly reduced.

The present nanostructure-based sequence methods remove the requirement for the nanostructure to identify each specific base. The polymerase in the current nanostructure-based sequencing methods functions precisely with respect to base identification, and does not simply slow down the movement of the nucleic acid through, on, or over the nanostructure. Instead, the nanostructure-based sequencing methods described herein depend on the bases provided to the polymerase, and use the translocation of the nucleic acids through, on, or over the nanostructure (e.g., the presence of absence of translocation, or a change in the rate or pattern of translocation) to determine the sequence.

Sequencing Conditions

It would be understood by those skilled in the art that a nanostructure-based sequencing complex can be generated in any of a number of different fashions. In one embodiment, promoter-bound target nucleic acid molecules (also referred to as templates or template nucleic acids) can be provided to a solid surface having polymerases immobilized thereon. In this embodiment, the target nucleic acid molecules can be fed through, on, or over the nanostructures before or after the target nucleic acid molecules are complexed with the immobilized polymerases. In another embodiment, the polymerases and the promoter-bound target nucleic acid molecules can be combined and then the polymerases immobilized on the solid surface. Similar to the previous embodiment, the target nucleic acid molecules can be fed through, on, or over the nanostructures before or after the polymerases are provided and subsequently immobilized. The order of complex formation will depend on several factors, including, for example, without limitation, whether or not a further moiety is attached to the end of the target nucleic acid molecule opposite the promoter-bound end.

The nanostructure-based sequencing described herein can be performed in an asynchronous (i.e., rate-limiting) mode or a synchronous (i.e., base-by-base) mode, or any combination thereof to determine the sequence of a target nucleic acid molecule. At a minimum, "sequencing conditions," as used herein, refers to the presence of at least one nucleoside triphosphate, which can be used as described below to determine the sequence of a target nucleic acid molecule. In addition to the presence of at least one nucleoside triphosphate as discussed in more detail herein, conditions under which sequencing reactions are performed are well known in the art. For example, appropriate buffer components (e.g., KCl, Tris-HCl, $MgCl_2$, DTT, Tween-20, BSA) can be used to provide a suitable environment for the enzyme. As used herein, nucleoside triphosphate refers to either the ribose-containing NTPs or the deoxyribose-containing dNTPs. Those skilled in the art would understand that the nucleoside triphosphates used in a particular sequencing reaction will be dictated by the particular polymerase(s).

a) Asynchronous Sequencing

The nanostructure-based sequencing method described herein can be used to sequence target nucleic acids based on an asynchronous incorporation of nucleotides. For asynchronous embodiments, the sequencing conditions under which the initial reaction occurs (i.e., first sequencing conditions) include the presence of four nucleoside triphosphates, where the nucleoside triphosphates are present in different amounts, at least one of which is rate-limiting and at least one of which is not rate-limiting. For example, one of the four nucleoside triphosphates is provided in a rate-limiting amount (e.g., in an amount that is less than the amount of the other three nucleoside triphosphates). In such a reaction, the polymerase will effectively pause each time it tries to incorporate the nucleoside triphosphate provided in the rate-limiting amount into the transcript, and such a pause can be observed in the pattern of movement as described herein.

Significantly, the number of bases between each pause can be precisely determined by detecting the cumulative amount of movement between pauses. Thus, the precise position of, for example, each guanine (G) nucleotide along the sequence of the target nucleic acid molecule can be concisely determined due to changes in the movement when the G nucleoside triphosphate is provided in rate-limiting amounts. Similar reactions can be performed under second, third and, if desired, fourth, sequencing conditions in which, respectively, the second, third, and fourth nucleoside triphosphate of the four nucleoside triphosphates is present in a rate-limiting amount. The combined information from the four reactions, whether they are performed simultaneously with one another or sequentially following one another, provide the complete sequence of the target nucleic acid molecule.

The pattern, even from a single reaction resulting in the positional sequence of one of four nucleotides can be compared to nucleic acid databases and used to identify the nucleic acid molecule with a high level of confidence. In addition, it would be understood by those skilled in the art that the sequence of a target nucleic acid molecule could be compiled using the positional information produced from three of the four nucleoside triphosphates, as the positional information of the fourth nucleotide in the sequence can be inferred once the other three nucleotides are known.

b) Synchronous or Base-by-Base Sequencing

The nanostructure-based sequencing method described herein can be used to sequence nucleic acids in a synchronous pattern, which otherwise might be known as base-by-base sequencing. For synchronous or base-by-base embodiments, the sequencing conditions under which the initial reaction occurs (i.e., first sequencing conditions) include the presence of a single nucleoside triphosphates. In such a reaction, transcription by the polymerase will only proceed if the target nucleic acid contains the complementary base at that position, which can be observed as a change in the movement of the nucleic acid as described herein. Such reaction conditions are continued until the movement does not change. It would be understood that the cumulative change in the movement can be used to precisely determine the number of times the first nucleoside triphosphate was sequentially incorporated into the nascent strand (e.g., in a homopolymeric region of the target nucleic acid molecule).

When a change is no longer observed in the movement of the nucleic acid under the first sequencing conditions (i.e., the presence of a first nucleoside triphosphate of the four nucleoside triphosphates), or if no changes in the movement are observed under the first sequencing conditions, a reaction is performed under second sequencing conditions. Second sequencing conditions include the presence of a second nucleoside triphosphate of the four nucleoside triphosphates. Changes in the movement of the nucleic acid through, on, or over the nanostructure are indicative of base incorporation into the nascent strand by the polymerase, while the absence of a change in the movement of the nucleic acid indicates that no base incorporation took place.

Such reactions, under first sequencing conditions, second sequencing conditions, third sequencing conditions (i.e., the presence of a third nucleoside triphosphate of the four nucleoside triphosphates) or fourth sequencing conditions (i.e., the presence of a fourth nucleoside triphosphate of the four nucleoside triphosphates), can be carried out in such a manner that the sequence of the target nucleic acid molecule is sequentially determined based on the changes in the movement of the nucleic acid under each of the respective sequencing conditions. It would be understood by those skilled in the art that steps can be taken to remove the residual nucleoside triphosphates under one sequencing condition before introducing a different sequencing condition. For example, the surface on which the polymerase is immobilized can be washed or flushed before introducing a different nucleoside triphosphate. While such washing steps are not required, it would be understood that such steps would increase the accuracy of the resulting sequence information.

c) Additional Sequencing Methodologies

The nanostructure-based sequencing methods described herein are amenable to a number of different variations and routine modifications, which can be utilized, for example, and without limitation, to further increase the accuracy of the sequencing information and further increase the amount of information obtained in a sequencing reaction.

For example, certain polymerases, usually RNA polymerases, possess a "strand-switching" or "turn-around" ability. This feature can be advantageously used in the methods described herein to increase the accuracy of the resulting sequence information. For example, when a polymerase reaches the end of a target nucleic acid, the polymerase can "jump" to the opposite strand and continue transcription. See, for example, McAllister at al. (US 2007/0077575) and Rong et al. (1998, J. Biol. Chem., 273(17):10253-60). In addition, certain RNA polymerases can "jump" from the double-stranded DNA template to the hybrid DNA-RNA transcript and resume transcription of the DNA strand. In addition, this type of recursive sequencing of a target nucleic acid molecule can be genetically engineered by introducing (e.g., ligating) a polymerase promoter onto each end of the target nucleic acid molecule, such that the polymerase binds and transcribes both strands.

In addition, one or more different polymerases (e.g., polymerases from different organisms or different polymerases from the same organism) can be immobilized onto a solid surface. As is known in the art, different polymerases recognize and bind to different promoter sequences. Therefore, one or more different polymerase promoters can be ligated to different populations of target nucleic acid molecules and a combined population of target nucleic acid molecules can be sequenced using the nanostructure-based sequencing methods described herein with the one or more different polymerases immobilized on the solid surface. By differentially-labeling, for example, the different polymerases or the different populations of target nucleic acid molecules (using, for example, beads emitting different wavelengths, fluorescent tags, or fluorescently-labeled antibodies), the sequence of one population of target nucleic acid molecules can be distinguished from the sequence of another population of target nucleic acid molecules. Using such methods, sequencing reactions on different populations of target nucleic acid molecules can take place simultaneously.

In some embodiments, both the polymerases and the populations of target nucleic acid molecules can be differentially labeled. It would be understood that labeling the target nucleic acid molecules can occur directly via the nucleic acid or, for example, via an additional moiety bound to the target nucleic acid molecule. This ability to differentially label at multiple levels of the sequencing reaction can be used, for example, to compare the processivity of different polymerases on target nucleic acid molecule having the same sequence, which may identify, for example, homopolymeric regions or regions of methylation, or to compare the polymerization of target nucleic acid molecules having different sequences by more than one polymerase.

Simply by way of example, any combination of polymerase enzymes (e.g., from one or more of the bacteriophages, one or more prokaryotes, or one or more eukaryotes), in conjunction with the appropriate nucleic acid promoter sequences, can be used in the nanostructure-based sequencing methods described herein. As discussed herein, this feature allows for a multiplexing of the sequencing reactions. Other variations that utilize different polymerases in conjunction with their specific promoter sequences as well as differential-labeling techniques are contemplated herein.

In some embodiments, two asynchronous nanostructure-based sequencing reactions can be performed under the same sequencing conditions (e.g., first sequencing conditions). Once sequencing has progressed for a sufficient number of nucleotides (e.g., at least 100 nt, 500 nt, 1,000 nt, 5,000 nt, or 10,000 nt or 20000 nt or 50000 nt or 100000 nt or 1500000 nt), the sequencing conditions of one of the reactions can be changed (e.g., to second sequencing conditions), and the nanostructure-based sequencing continued. The resulting sequence information obtained under the first sequencing conditions can be used to align a particular target nucleic acid molecule in the first reaction with the same particular target nucleic acid molecule in the second reaction, which, when the sequencing conditions are changed, allows positional sequence information to be obtained for two nucleotides within a particular target nucleic acid molecule.

Those skilled in the art would understand that the size of the nanostructures and/or the ionic content of the buffers around the nanostructures can affect the efficiency and accuracy of the sequencing reaction, particularly since polymerase enzymes place torsion on the nucleic acid molecules during elongation and translocation. In some instances, there may be polymerases and/or sequencing conditions in which loading of the polymerases and/or the nanostructures can be used to advantageously affect the rate of sequencing, although in most cases, those skilled in the art would prefer to minimize these effects.

Articles of Manufacture/Kits

Articles of manufacture (e.g., kits) are provided herein. An article of manufacture can include a solid substrate, as discussed herein, onto which a plurality of polymerase enzymes is immobilized. A plurality of polymerase enzymes refers to at least 10 polymerases (e.g., at least 20, 50, 75, or 100 enzymes), at least 100 polymerases (e.g., at least 200, 500, or 1,000 enzymes), or at least 1,000 polymerases (e.g., at least about 2,500, 5,000, 10,000, 50,000 enzymes or more).

Articles of manufacture are well known in the art and can include packaging material (e.g., blister packs, bottles, tubes, vials, or containers) and, in addition to the solid surface having polymerases immobilized thereon, can include one or more additional components.

In some embodiments, an article of manufacture can include nucleic acid sequences corresponding to a polymerase promoter. As discussed herein, promoters that direct transcription by polymerases are well known and used routinely in the art.

In some embodiments, an article of manufacture can include a tether. As discussed herein, a tether can be used to attach target nucleic acid molecules to a moiety (e.g., a tag). In some embodiments, a tether includes nucleic acid sequences, which, for example, can be biotinylated, such that they bind to, for example, streptavidin-labeled tags.

In some embodiments, an article of manufacture can include one or more nucleoside triphosphates. When more than one nucleoside triphosphate is provided, they can be provided in combination (e.g., in a single container) or separately (e.g., in separate containers).

In some embodiments, an article of manufacture further includes instructions. The instructions can be provided in paper form or in any number of electronic forms (e.g., an electronic file on, for example, a CD or a flash drive, or directions to a site on the internet (e.g., a link). Such instructions can be used to identify movement of the nucleic acid through, on, or over the nanostructure, compile the sequence of a target nucleic acid molecule based on the movement and the presence of a nucleoside triphosphate; and/or apply an appropriate tension on the nucleic acid.

Nanostructure-Based Sequencing Systems

A nanostructure-based sequencing system as described herein includes at least a Sequencing Module. A Sequencing Module for sequencing target nucleic acid molecules typically includes a receptacle for receiving a solid substrate, a tension source for providing directional force, and means for determining changes in an electric current across the nanostructures. The solid substrate and the tension source are discussed above, and means for determining or detecting a change in an electric current are well-known in the art. Such means can include, for example, using ionic current measurement (using, e.g., a voltage clamp amplifier (e.g., Axopatch)) or using transverse electric fields (e.g., dragging, tunneling) (e.g., Tsutsui et al., 2012, Sci. Rep., 2:394). A receptacle for receiving a solid substrate can be configured, for example, as a recessed chamber. A Sequencing Module also can include a computer processor or means to interface with a computer processor. Further, primary analysis software can be provided as part of a Sequencing Module.

In addition, a Sequencing Module further can include a heating and cooling element and a temperature control system for changing and regulating the temperature of the sequencing reactions. In addition, a Sequencing Module further can include fluidics (e.g., one or more reagent or buffer reservoirs and tubing for delivering the one or more reagents or buffers to the reaction chamber). Fluidics for delivering one or more reagents or buffers also can include, without limitation, at least one pump. Without limitation, exemplary reagents that can be used in a sequencing reaction can include, for example, nucleoside triphosphates and/or enzymes (polymerase). Also without limitation, exemplary buffers that can be used in a sequencing reaction can include, for example, of a wash buffer, an enzyme-binding buffer and a sequencing buffer.

The nanostructure-based sequencing systems described herein can significantly advance point-of-care diagnostics and genomics based on massively parallel single molecule analysis with the single nucleotide resolution. The system is intrinsically suited for highly multiplexed target identification and has unlimited flexibility of being able to be reconfigured to interrogate simultaneously or sequentially different nucleic acid targets, e.g. pathogens and human biomarkers. Current PCR- and microarray-based methods of sequencing nucleic acids are limited by being able to detect only known sequences or infectious agent(s) because of the specific set of reagents (primers and probes) required for positive identification.

For a system designed, for example, for high-throughput clinical diagnostics or for point-of care diagnostics, a nanostructure-based sequencing system as described herein can be coupled with a Sample Preparation Module and a Template Finishing Module.

A Sample Preparation Module can be configured to lyse cells, thereby releasing the nucleic acids, and a Sample Preparation Module also can have the capability of shearing/fragmenting the nucleic acid. A Sample Preparation Module typically includes a receptacle for receiving a biological sample, and fluidics for delivering one or more reagents or buffers to the biological sample. A Sample Preparation Module can be configured to receive a variety of different biological samples or a Sample Preparation Module can be configured to receive a specific type of biological sample (e.g., a swab, a tissue sample, a blood or plasma sample, saliva, or a portion of a culture) or a biological sample provided in a specific form (e.g., in a vial or tube or on blotting paper). A Sequencing Preparation Module also can be configured to capture certain molecules from the biological sample (e.g., bacterial cells, viruses, etc.) using, for example, filters, columns, magnets, immunological methods, or combinations thereof (e.g., Pathogen Capture System, NanoMR Inc.).

A Sample Preparation Module can include reagents or buffers involved in obtaining the nucleic acids from a biological sample and preparing the nucleic acids for sequencing. For example, reagents involved in obtaining nucleic acids for sequencing include cell lysis reagents, nucleic acid cleavage enzymes, DNA polymerases, oligonucleotides, and/or DNA binding agents (e.g., beads or solid matrices to bind and wash the target nucleic acid molecules), while buffers involved in obtaining nucleic acids for sequencing include lysis buffer, wash buffer, elution buffer, or binding buffer. Many of the functional components of a Sample Preparation Module are commercially available (e.g. Silica gel membrane (Qiagen or Ambion kits) or as an integrated part of Palladium System (Integrated Nano Technologies Inc.)). In addition, as an alternative to enzymatic cleavage of nucleic acid templates, instruments that fragment nucleic acids are commercially available (e.g., Covaris).

A Template Finishing Module can be configured to attach polymerase promoter sequences to target nucleic acid molecules. A Template Finishing Module typically includes fluidics for delivering one or more reagents or buffers to the target nucleic acid molecules. For example, a Template Finishing Module can include reagents and buffers for the purpose of ligating polymerase promoter sequences to the target nucleic acid molecules. For example, reagents involved in ligating promoter sequences to target nucleic acid molecules include, obviously, the promoter sequences, but also can include, for example, ligase enzymes, a tether or PCR reagents, while buffers involved in ligating promoter sequences to target nucleic acid molecules include ligation buffer, enzyme-binding buffer, washing buffer and sequencing buffer.

Depending upon the configuration of the nanostructure-based sequencing system as described herein, the plurality of polymerases can be immobilized on the solid surface prior to introducing the promoter-bound target nucleic acid molecules. Alternatively, a plurality of polymerases can be combined with the promoter-bound target nucleic acid molecules and the entire complex deposited on the solid surface. The latter procedure is feasible because the binding kinetics for polymerases and their corresponding promoter sequences is very fast, efficient and specific.

Sequence Determination Following Nanostructure-Based Sequencing

Figure 4:
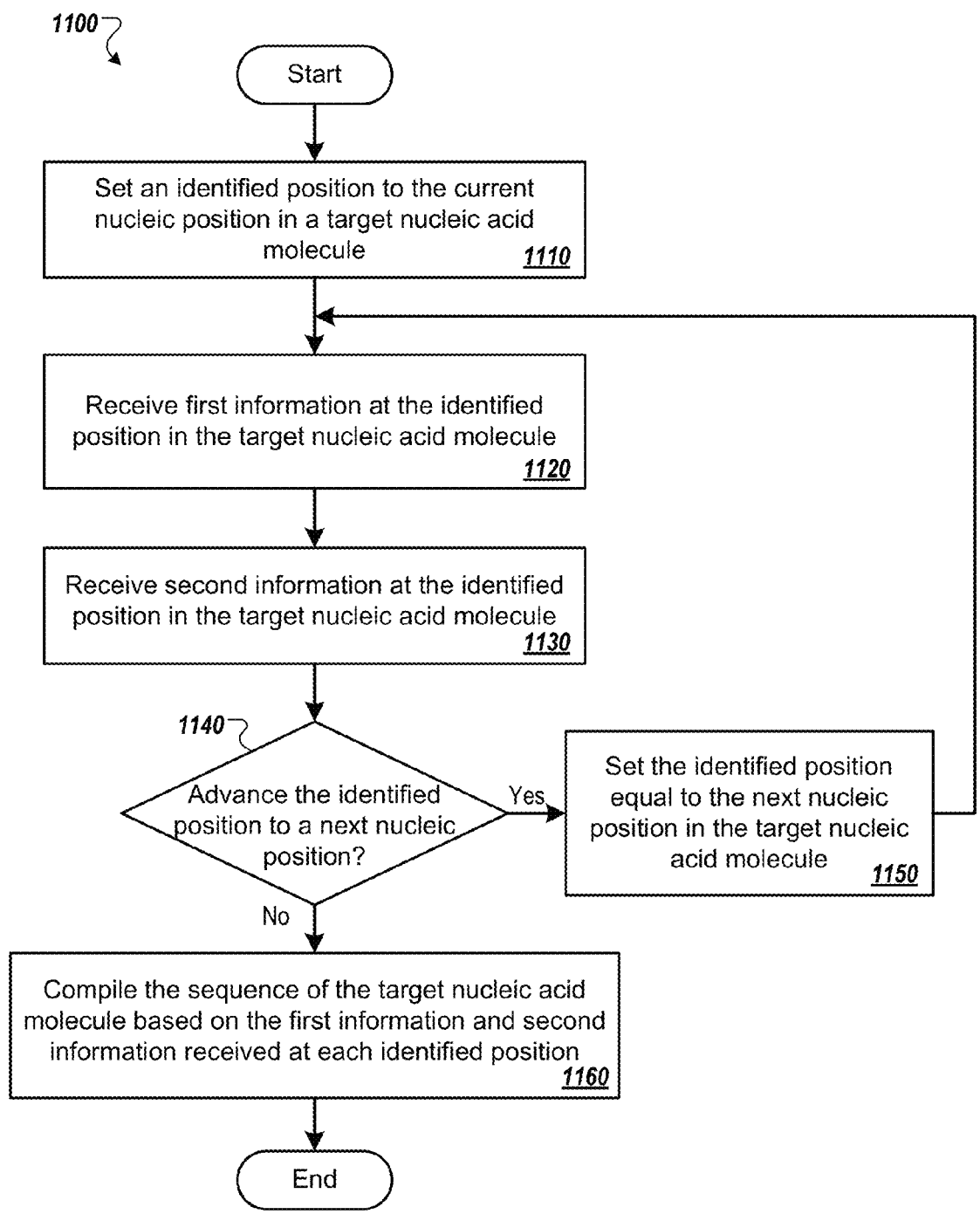
FIG. 4 is a flow diagram illustrating an example process for determining the sequence of a target nucleic acid molecule.
Figure 5:
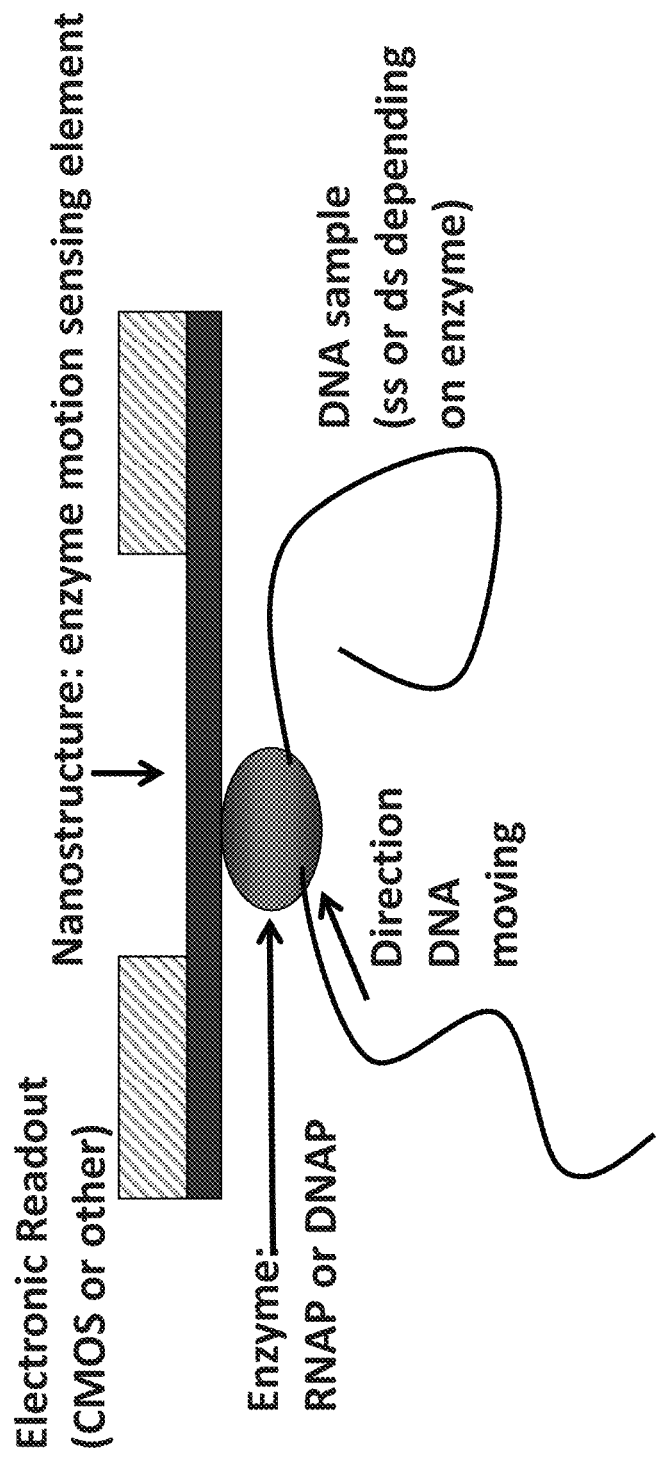
FIG. 5 shows an embodiment of a single-molecule nanostructure-based sequencing complex that can utilize either a DNA polymerase or a RNA polymerase. The enzyme is attached to a functionalized solid surface of, in this embodiment, a nanotube (e.g., a Carbon nanotube). Sequencing is performed as described herein and the nucleic acid is translocated through the nanostructure. Electrical signals that result from changes in the ionic concentration around the enzyme and near the nanostructure (e.g., in the Debye region) are measured. Since the polymerase enzyme adopts various conformations as it interacts with the template and incorporates bases into the nascent strand, the electronic signal through the nanotube can be used to correlate the motion, location and/or shape of the enzyme. Thus, when the enzyme pauses in the presence of one nucleotide in a rate-limiting amount, the electronic signal shows characteristics of pausing.

FIG. 4 is a flow diagram illustrating an example process 1100 for determining the sequence of a target nucleic acid molecule. In some examples, the process 1100 can be implemented using one or more computer program applications executed using one or more computing devices. For purposes of illustration, a non-limiting example context is provided that is directed to determining the sequence of a target nucleic acid molecule based upon data obtained during elongation of the target nucleic acid molecule by the polymerase.

The process 1100 starts by setting an identified position to the current nucleic position in a target nucleic acid molecule (1110) being sequenced using the nanostructure-based sequencing described herein. An identified position can be, for example, the first nucleotide incorporated/elongated within the promoter sequence, the first nucleotide incorporated/elongated from the target nucleic acid molecule (i.e., after the promoter sequences), or any nucleotide position along a target nucleic acid molecule.

First datum (i.e., first information) at the identified position in the target nucleic acid molecule is received (1120) from the nanostructure-based sequencing system or provided based upon information from the operation of the nanostructure-based sequencing, and second information (i.e., second datum) at the identified position in the target nucleic acid molecule is provided or received (1120). For example, the first datum can be information regarding translocation (i.e., movement) of the nucleic acid through, on, or over a nanostructure. For example, first datum can be a rate of translocation, a determination of the presence or absence of translocation, or a change in an established pattern of translocation. For example, the second datum can be information regarding the presence and/or availability (e.g., concentration) of one or more nucleoside triphosphates in the sequencing reaction.

The nucleotide at an identified position then can be determined based upon the first and second data. For example, if the first datum indicates a change in the rate of translocation and the second datum indicates the presence of guanine nucleoside triphosphate in the reaction, then the nucleotide at the identified position in the target nucleic acid molecule is determined to be cytosine. Similarly, if the first datum indicates an absence of change in the rate of translocation and the second datum indicates the presence of guanine nucleoside triphosphate in the reaction, the nucleotide at the indicated position in the target nucleic acid molecule is determined to be non-guanine (i.e., adenine, guanine, or thymine).

If it is determined that the identified position can be advanced to a next position (1140), the identified position is set equal to the next nucleic position in the target nucleic acid molecule (1150) and the process 1100 continues (1120). If it is determined that the identified position cannot be advanced to a next position (1140), the sequence of the target nucleic acid molecule based on the first information and second information received at each identified position is compiled (1160) and the process 1100 ends. The identified position cannot be advanced to a next position when elongation can no longer occur due, for example, to completion of polymerization of the target nucleic acid molecule or expiration of polymerase activity (e.g., due to decay of enzyme activity).

Embodiments of the subject matter and the operations described in this specification can be implemented in digital electronic circuitry, or in computer software, firmware, or hardware, or in combinations of one or more of them. Embodiments of the subject matter described herein can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, a mobile communication device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described herein can be implemented as operations performed by a data processing apparatus on data stored on one or more computer-readable storage devices or received from other sources. The term "data processing apparatus" encompasses all kinds of apparatus, devices, and machines for processing data including, by way of example, a programmable processor, a mobile communications device, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile communications device, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Solid Surface Preparation

An NTA monolayer was prepared as described (see Paik et al., 2005, *Chem. Commun.*, 15:1956-58. Ni-NTA surfaces were obtained by immersing the NTA-functionalized substrates into 10 mM Tris-HCl buffer (pH 8.0) containing 0.1

M NiCl$_2$ for 30 min. The substrates were then rinsed several times with Milli-Q water and dried under a nitrogen stream.

The freshly cleaned substrates were immersed into a distilled toluene solution containing 1% (v/v) 3-glycidyloxypropyl trimethoxysilane under argon for 2 days. After the substrates were removed from the solution, they were rinsed with distilled toluene and dried under a nitrogen stream. The substrates functionalized with epoxy-terminated SAM were incubated in 10 mM Tris-HCl buffer (pH 8.0) containing 2.5 mM N,N bis(carboxymethyl)-L-lysine (NTA) at 60° C. for 4 h. The substrates were rinsed with Milli-Q water and dried in preparation for microcontact printing.

A limited nonspecific binding effect of His-tagged protein to the NTA SAM was observed, demonstrating the NTA SAM to be a suitable surface for fabricating Ni(II) ion patterns with microcontact printing and dip-pen nanolithography techniques.

Example 2

Cloning and Purification of His-Tagged RNA Polymerase

A DNA fragment that encodes the 38 amino acid SBP-tag was synthesized by PCR using pTAGk19 as a template and synthetic DNA oligomers RP46 and RP47 (see below) as primers. The fragment was digested with NcoI and ligated into pBH16117, resulting in pRP6.

SBP-His-RNA polymerase and His-RNA polymerase were expressed and purified as previously described (He et al., 1997, *J. Protein Expression Purif.*, 9:142-51; and Keefe et al, 2001, *J. Protein Expression Purif.*, 23:440-46).

Example 3

Immobilization of Polymerase

The following reaction scheme was followed for the immobilization of RNA polymerase molecules on Si(111): (a) 40% NH$_4$F, 10 min, 25° C.; (b) Cl$_2$ gas, 20 min, 100° C.; (c) mPEG, over-night, vacuum, 150° C.; (d) DSC, DEIDA, DMAP, DMF, overnight, 25° C.; (f) BBTO, diethyl ether, 6 h, 25° C.; (g) CuSO$_4$, ethanol 20 min, 25° C.; (h) 6×His-tagged protein incubation.

Example 4

Microcontact Printing (μCP) and Complex Formation

A 10:1 (v/v) mixture of poly(dimethylsiloxane) (PDMS) and curing agent (Sylgard 184, Dow Corning) was cast against a patterned silicon master to prepare PDMS stamps with 5 micron line features, with a spacing of 3 and 10 micron line features and a spacing of 5 micron. The non-oxidized PDMS stamps were incubated in 10 mM Tris-HCl buffer (pH 8.0) containing 0.1 M NiCl$_2$ for about 1 h and then dried with a nitrogen stream. The stamps were brought into contact with a NTA-terminated substrate for 3 min. After peeling off the stamp, the Ni(II)-printed substrates were incubated in about 200 μL of 25 mM Tris-HCl buffer (pH 7.5) containing 100 nM of His-T7 RNAP with ds-DNA, promoter and magnetic tags attached via streptavidin-biotin bonds for 30 min and then rinsed with 10 mM Tris-HCl buffer (pH 8.0) and Milli-Q water to remove excess protein.

Example 5

Tethering 2.8 micron SA-conjugated beads (Dynal) and 1.0 micron biotinylated beads were diluted (1:20 and 1:200, respectively) in PBS, and mixed at room temperature for 15 min. Coverslips were coated with Ni2+-NTA HRP conjugate (QIAGEN) and flow chambers were assembled by aligning together slightly separated coverslips as previously described (see, Noji et al., 1997, *Nature*, 386:299-302).

Example 6

Template Preparation

DNA template for Sequencing by transcription was prepared by joining together 4.6 kb phage T7 DNA fragment bearing T7 promoter and 0.5 kb biotinylated fragment of Lambda DNA. A 4.6 kb fragment was generated by PCR using #T7pPK13 forward primer and # T7phi17REV primer containing an XbaI recognition site at the 3'end. A 0.5 kb PCR fragment was generated by PCR using #F3 and #R3 primers in the presence of Biotin-16-dUTP (Roche). After PCR was completed, the purified PCR product was digested with NheI and cleaned up with QIAquick PCR Purification Kit (QIAGEN).

After digestion of the PCR product with XbaI, the 4.6 kb piece was joined by overnight ligation at 15° C. with a 0.5 kb biotinylated PCR fragment digested with NheI. The resulting ligation product of 5.1 kb was resolved using 0.7% agarose gel electrophoresis and extracted from the gel using QIAquick Gel Extraction Kit (QIAGEN). This DNA was used in the transcription and sequencing experiments.

The following primers were used for PCR: # T7pPK13: GCA GTAATACGACTCACTATA GGG AGA GGG AGG GAT GGA GCC TTT AAG GAG GTC AAA TGG CTA ACG (SEQ ID NO:1; the T7 promoter sequence is underlined, the bold G is +1 and the bold C is a pause site at position+20); # T7phi17REV: GGC A-T CTA GA- TGC ATC CCT ATG CAG TCC TAA TGC (SEQ ID NO:2; contains Xba site); #F3: GGC AGC TAG CTA AAC ATG GCG CTG TAC GTT TCG C (SEQ ID NO:3; contains NheI restriction site at 5' end); and #R3: AGC CTT TCG GAT CGA ACA CGA TGA (SEQ ID NO:4).

The following table shows the reaction mixture used to prepare a 4.6 Kb fragment from T7 phage containing the T7 promoter. PCR amplification was performed under the following cycling conditions: 94° C. for 30", 32 cycles at 94° C. for 10", 55° C. for 30", 65° C. for 4'10", 65° C. for 10', followed by a 4° C. hold.

| Component | Volume |
| --- | --- |
| 5x LongAmp Buffer with Mg (New England Biolabs) | 60 μl |
| 25 mM NTPs (each) | 3.6 ul |
| 10 mM # T7pPK13 | 12 μl (0.4 mM final) |
| 10 mM #T7phi17REV | 12 μl (0.4 mM final) |
| (50 ng/μl) | 6 μl |
| H$_2$O | 194.4 μl |
| LongAmp Polymerase (NEB) | 12 μl |
| Total Reaction Volume | 300 μl |

The following table shows the reaction mixture used to prepare a 0.5 Kb lambda fragment containing multiple biotins. PCR amplification was performed under the following cycling conditions: 94° C. for 10', 32 cycles at 94° C. for 10", 55° C. for 30", 72° C. for 1', 72° C. for 7', followed by a hold at 4° C.

| Component | Volume |
|---|---|
| 10x TaqGold buffer w/o Mg (Applied Biosystems) | 10 μl |
| 10 μM F3 | 6 μl |
| 10 μM R3 | 6 μl |
| 25 mM MgCl$_2$ | 10 μl |
| Lambda DNA (50 ng/μl) | 2 μl |
| 1 mM dGTP | 10 μl |
| 1 mM dCTP | 10 μl |
| 1 mM dATP | 10 μl |
| 1 mM dTTP | 6.5 μl |
| 1 mM Bio-16-dUTP | 3.5 μl |
| H$_2$O | 21 μl |
| TagGold Pol | 5 μl |
| Total Reaction Volume | 100 μl |

Example 7

Complex Formation and Sequencing Reaction

A PEG-Cu$^{++}$ functionalized glass slide (MicroSurfaces, Inc) was passivated with Buffer B+1% BSA.

The following reaction was set up at room temperature and incubated for 3 min at 37° C.

| Component | Volume |
|---|---|
| 10x Buffer A | 0.5 μl |
| Template (5.1 kb PT7pK13-Bio DNA) 6 ng/μl, 1.93 fmoles/μl, or 2 nM (final 0.8 nM) | 2 μl |
| 10x mix of three NTP (0.3 mM ATP + 0.3 mM GTP + 0.1 mM UTP) | 1 μl |
| 4 μM His-T7RNAP (final 0.8 μM; prepared from stock by diluting in Buffer A) | 1 μl |
| H$_2$O | 0.5 μl |
| Total Reaction Volume | 5 μl |

45 μl of Buffer B was added to the reaction mix with T7 RNAP-DNA elongation complexes halted at position+20 of the template, and the mixture was infused into the flow cell over a period of 5 min.

The flow cell was washed with Buffer B, and 1 μm SA magnetic beads (46 μl Buffer B+0.1% BSA mixed with 6 μl washed beads in Buffer B+0.1% BSA) was infused over a period of 12 min. The flow cell was washed with Buffer B+0.1% BSA.

0.8 micron polystyrene biotinylated beads (2 μl of washed beads+48 μl 1×B/0.1% BSA) were infused into the flow cell and incubated for 15 min to form bi-particles with surface tethered magnetic SA beads. The flow cell was washed with Buffer B to remove unbound 0.8 micron polystyrene beads.

Transcription/sequencing was started by infusing Buffer B+250 μM NTPs+10 mM DTT into the flow cell. Four different NTP mixes (each containing less of one of the nucleotides) were used in four different flow cells.

| 1x Buffer A |
|---|
| 20 mM Tris pH 8.0 |
| 14 mM MgCl2 |
| 10 mM DTT |
| 0.1 mM EDTA |
| 20 mM NaCl |
| 1.5% glycerol |
| 20 μg/ml BSA |

| 1x Buffer B |
|---|
| 20 mM Tris pH 8.0 |
| 4 mM MgCl2 |
| 0.1 mM DTT |
| 0.1 mM EDTA |
| 20 mM NaCl |
| 20 μg/ml BSA |

It is to be understood that, while the systems, methods and compositions of matter have been described herein in conjunction with a number of different aspects, the foregoing description of the various aspects is intended to illustrate and not limit the scope of the systems, methods and compositions of matter. Other aspects, advantages, and modifications are within the scope of the following claims.

Disclosed are systems, methods and compositions that can be used for, can be used in conjunction with, can be used in preparation for, or are products of the disclosed systems, methods and compositions. These and other materials are disclosed herein, and it is understood that combinations, subsets, interactions, groups, etc. of these systems, methods and compositions are disclosed. That is, while specific reference to each various individual and collective combinations and permutations of these compositions and methods may not be explicitly disclosed, each is specifically contemplated and described herein. For example, if a particular system part, composition of matter or particular method is disclosed and discussed and a number of system parts, compositions or methods are discussed, each and every combination and permutation of the system parts, compositions and methods are specifically contemplated unless specifically indicated to the contrary. Likewise, any subset or combination of these is also specifically contemplated and disclosed.

What is claimed is:

1. A method of determining the sequence of a target nucleic acid molecule, comprising:
   providing a nanotube having a polymerase immobilized on or in the vicinity of said nanotube;
   contacting a polymerase with a double-stranded naturally occurring target nucleic acid molecule under first sequencing conditions, wherein the first sequencing conditions comprise the presence of nucleoside triphosphates consisting of four nucleoside triphosphates that each lack a detectable label, wherein a first nucleoside triphosphate of the four nucleoside triphosphates is present in a rate-limiting amount;
   detecting a pause in the movement of the target nucleic acid molecule and/or one or more nascent strand(s) on or over the nanotube due to a pause in translocation of the target nucleic acid molecule and/or one or more nascent strand(s) by the polymerase;
   repeating the contacting and detecting steps under second sequencing conditions or third sequencing conditions, both comprising the presence of nucleoside triphosphates consisting of four nucleoside triphosphates that each lack a detectable label, wherein a second nucleoside triphosphate of the four nucleoside triphosphates is present in a rate-limiting amount in the second sequencing conditions and wherein a third nucleoside triphosphate of the four nucleoside triphosphates is present in a rate-limiting amount; and
   determining the sequence of the target nucleic acid molecule based on the pause(s) in the movement of the target nucleic acid molecule and/or one or more nascent strand(s) on or over the nanotube detected under the first, second, and third sequencing conditions, wherein the pause(s) in movement indicate the presence of the rate-limiting nucleotide at that position.

2. The method of claim 1, wherein the solid substrate is glass.

3. The method of claim 1, wherein the polymerase is a RNA polymerase.

4. The method of claim 3, wherein the RNA polymerase is selected from the group consisting of a bacteriophage RNA polymerase and a bacterial RNA polymerase.

5. The method of claim 4, wherein the bacteriophage RNA polymerase is selected from the group consisting of a T7 RNA polymerase and a T3 RNA polymerase.

6. The method of claim 4, wherein the bacterial RNA polymerase is an *E. coli* RNA polymerase.

7. The method of claim 1, wherein the polymerase is a DNA polymerase.

8. The method of claim 7, wherein the DNA polymerase is selected from the group consisting of phi29, T7 DNA polymerase, *Bacillus subtilis* DNA polymerase, and Taq DNA polymerase.

9. The method of claim 1, wherein the target nucleic acid molecule further comprises a magnetic tag.

10. The method of claim 1, wherein the detecting step comprises measuring a change in electric current of the nanotube.

11. The method of claim 1, wherein the detecting step comprises measuring a change in ionic conduction of the nanotube.

12. The method of claim 1, wherein the detecting step further comprises capturing movement on a CMOS based manufactured nanotube and electronics.

13. The method of claim 1, further comprising:
repeating the contacting and detecting steps under fourth sequencing conditions comprising the presence of nucleoside triphosphates consisting of four nucleoside triphosphates that each lack a detectable label, wherein a fourth nucleoside triphosphate of the four nucleoside triphosphates is present in a rate-limiting amount a plurality of times; and
determining the sequence of the target nucleic acid molecule based on the pause(s) in the movement of the target nucleic acid molecule and/or one or more nascent strand(s) on or over the nanotube detected in the first, second, third, and fourth sequencing conditions.

14. The method of claim 1, wherein the position in the target nucleic acid molecule is determined by detecting the cumulative amount of movement.

15. A method of determining the sequence of a target nucleic acid molecule, comprising:
providing a nanotube, wherein a polymerase is immobilized on or near the nanotube;
contacting the polymerase with the target nucleic acid molecule under first sequencing conditions comprising the presence of nucleoside triphosphates consisting of four nucleoside triphosphates, where a first nucleoside triphosphate of the four nucleoside triphosphates is present in a rate-limiting amount;
detecting a pause in the movement of the target nucleic acid molecule and/or one or more nascent strand(s) on or over the nanotube due to a pause in translocation of the target nucleic acid molecule and/or one or more nascent strand(s) by the polymerase;
contacting the polymerase with the target nucleic acid molecule under second sequencing conditions comprising the presence of nucleoside triphosphates consisting of four nucleoside triphosphates, where a second nucleoside triphosphate of the four nucleoside triphosphates is present in a rate-limiting amount;
detecting a pause in the movement of the target nucleic acid molecule and/or one or more nascent strand(s) on or over the nanotube due to a pause in translocation of the target nucleic acid molecule and/or one or more nascent strand(s) by the polymerase;
contacting the polymerase with the target nucleic acid molecule under third sequencing conditions comprising the presence of nucleoside triphosphates consisting of four nucleoside triphosphates, where a third nucleoside triphosphate of the four nucleoside triphosphates is present in a rate-limiting amount;
detecting a pause in the movement of the target nucleic acid molecule and/or one or more nascent strand(s) on or over the nanotube due to a pause in translocation of the target nucleic acid molecule and/or one or more nascent strand(s) by the polymerase;
determining positional information of the first, second, and third nucleoside triphosphates along the target nucleic acid molecule based on the pause(s) in the movement of the target nucleic acid molecule and/or one or more nascent strand(s) on or over the nanotube, wherein the pause(s) in movement indicate the presence of the rate-limiting nucleotide at that position.

16. The method of claim 15, further comprising:
contacting the polymerase with the target nucleic acid molecule under fourth sequencing conditions comprising the presence of nucleoside triphosphates consisting of four nucleoside triphosphates, where a fourth nucleoside triphosphate of the four nucleoside triphosphates is present in a rate-limiting amount;
detecting a pause in the movement of the target nucleic acid molecule and/or one or more nascent strand(s) on or over the nanotube due to a pause in translocation of the target nucleic acid molecule and/or one or more nascent strand(s) by the polymerase;
determining positional information of the first, second, third, and fourth nucleoside triphosphates along the target nucleic acid molecule based on the pause(s) in the movement of the target nucleic acid molecule and/or one or more nascent strand(s) on or over the nanotube.

* * * * *

UNITED STATES PATENT AND TRADEMARK OFFICE
CERTIFICATE OF CORRECTION

PATENT NO. : 9,725,763 B2  
APPLICATION NO. : 14/185469  
DATED : August 8, 2017  
INVENTOR(S) : Theofilos Kotseroglou and Stephanos Papademetriou Page 1 of 1

It is certified that error appears in the above-identified patent and that said Letters Patent is hereby corrected as shown below:

On the Title Page

Item (72):
In Column 1 (inventors) Line 1 Delete "Kosteroglou," and insert --Kotseroglou,--, therefor.

Signed and Sealed this  
Tenth Day of November, 2020

Andrei Iancu  
*Director of the United States Patent and Trademark Office*